United States Patent
Erickson et al.

(10) Patent No.: US 6,368,350 B1
(45) Date of Patent: Apr. 9, 2002

(54) INTERVERTEBRAL DISC PROSTHESIS AND METHOD

(75) Inventors: Richard A. Erickson, Edina; Steven L. Griffith, Eden Prairie, both of MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 0 days.

(21) Appl. No.: 09/266,369

(22) Filed: Mar. 11, 1999

(51) Int. Cl.$^7$ ................................................ A61F 2/44
(52) U.S. Cl. ................................ 623/17.14; 623/17.11; 623/17.15; 623/17.16
(58) Field of Search ........................ 623/16, 17, 18, 623/16.11, 17.11, 17.14, 17.15, 17.16, 18.11

(56) References Cited

U.S. PATENT DOCUMENTS

| | | |
|---|---|---|
| 4,759,766 A | 7/1988 | Buettner-Janz et al. |
| 4,759,769 A | 7/1988 | Hedman et al. |
| 4,911,718 A | 3/1990 | Lee et al. |
| 4,946,378 A | 8/1990 | Hirayama et al. |
| 4,955,908 A | 9/1990 | Frey et al. |
| 5,047,055 A | 9/1991 | Bao et al. |
| 5,071,437 A | 12/1991 | Steffee |
| 5,123,926 A | 6/1992 | Pisharodi |
| 5,258,031 A | 11/1993 | Salib et al. |
| 5,401,269 A | 3/1995 | Buttner-Janz et al. |
| 5,425,773 A | 6/1995 | Boyd et al. |
| 5,507,816 A * | 4/1996 | Bullivant ................. 623/17.15 |
| 5,556,431 A | 9/1996 | Buttner-Janz |
| 5,676,701 A | 10/1997 | Yuan et al. |
| 5,888,226 A * | 3/1999 | Rogozinski |
| 6,039,763 A * | 3/2000 | Shelokov .................... 623/17 |
| 6,113,637 A * | 9/2000 | Gill et al. |

FOREIGN PATENT DOCUMENTS

| | | | |
|---|---|---|---|
| EP | 566810 | * 10/1993 | ................. 623/17 |
| EP | 0 747 025 A1 | 12/1996 | |
| FR | 2 718 635 | 10/1995 | |
| FR | 2 730 159 | 8/1996 | |
| WO | 94/04100 | * 3/1994 | ................. 623/17 |

OTHER PUBLICATIONS

Bogduk et al., "A biological basis for instantaneous centres of rotation of the vertebral column," *Proc. Inst. Mech. Eng.* [H], 209(3):177–83 (1995).

Gertzbein et al., "Centrode Patterns and Segmental Instability in Degenerative Disc Disease," *Spine*, 10(3):257–61 (1985).

Griffith et al., "A Multicenter Retrospecitve Study of the Clinical Results of the LINK® SB Charite Intervertebral Prosthesis," *Spine*, 19(16):1842–1849 (1994).

Haher et al., "Instantaneous axis of rotation as a function of the three columns of the spine," *Spine*, 17(6):S149–54 (Jun. 1992).

Haher et al., "The effect of the three columns of the spine on the instantaneous axis of rotation in flexion and extension," *Spine*, 16(8): S312–18 (Aug. 1991).

(List continued on next page.)

Primary Examiner—Jeffrey A. Smith
(74) Attorney, Agent, or Firm—Merchant & Gould P.C.

(57) ABSTRACT

The present invention is directed to intervertebral prosthetic devices and methods. The intervertebral prosthetic devices and methods of the invention provides a variable instantaneous axis of rotation. In general, the disclosed devices include two bearing surfaces, a first bearing surface being curved and a second bearing surface being planar. In some embodiments, the curved bearing surface provides at least three degrees of rotational freedom and the planar bearing surface provides at least two degrees of translational freedom and one degree of rotational freedom. Several embodiments with varying degrees of rotational or translational freedom are disclosed.

29 Claims, 12 Drawing Sheets

OTHER PUBLICATIONS

Klein et al., "Relocation of the bending axis during flexion—extension of lumbar intervertebral discs and its implications for prolapse," *Spine*, 8(6):659–64 (Sep. 1983).

Kostuik, John P., "Alternatives to Spinal Fusion," *Orthopedic Clinics of North America*, 29(4):701–15 (Oct. 1998).

Liu et al., "A new technique for the three—dimensional study of the spine in vitro and in vivo by using a motion—analysis system," *J. Spinal Disord.*, 10(4):329–38 (Aug. 1997).

Pearcy et al., "Instantaneous axes of rotation of the lumbar intervertebral joints," *Spine*, 13(9):1033–41 (Sep. 1988).

Seligman et al., Computer analysis of spinal segment motion in degenerative disc disease with and without axial loading, *Spine*, 9(6):566–73 (Sep. 1984).

Yoshioka et al., "Motion characteristic of the normal lumbar spine in young adults; instantaneous axis of rotation and vertebral center motion analyses," *J. Spinal Disord.*, 3(2):103–13 (Jun. 1990).

White et al., "Part 1: Scoliosis, Anatomic Considerations," *Clinical Biomechanics of the SPINE*, Second Edition, pp. 128–130 (1978).

* cited by examiner

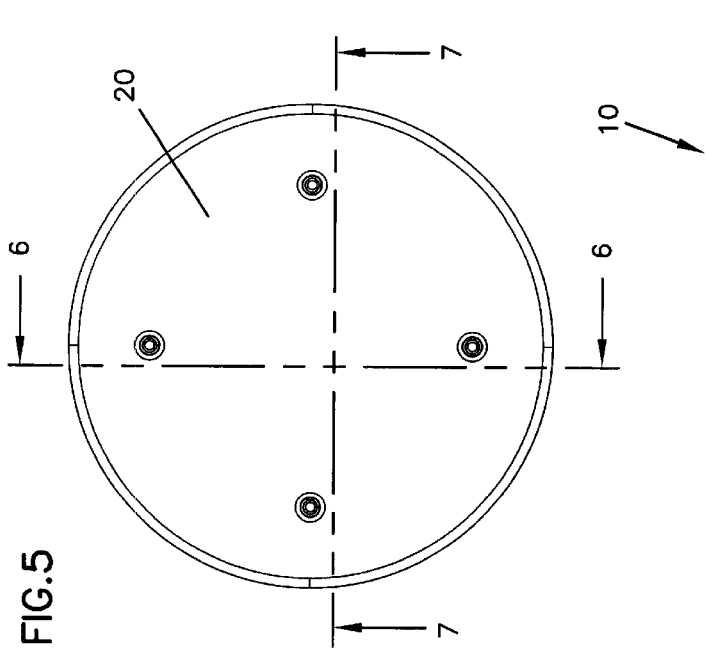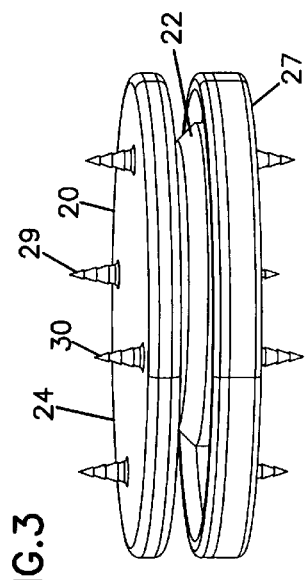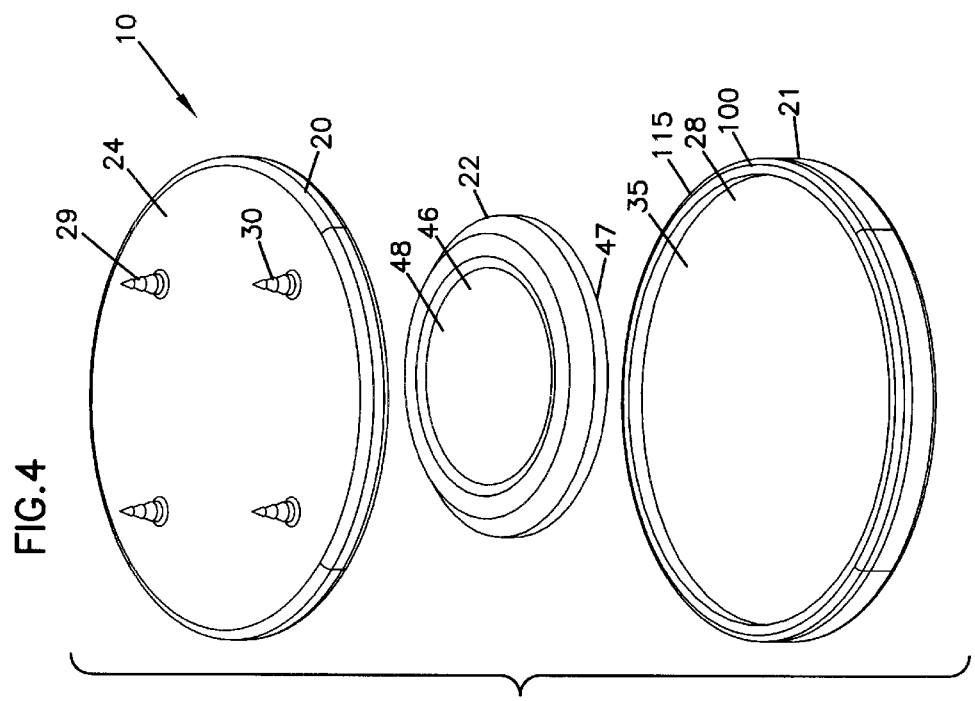

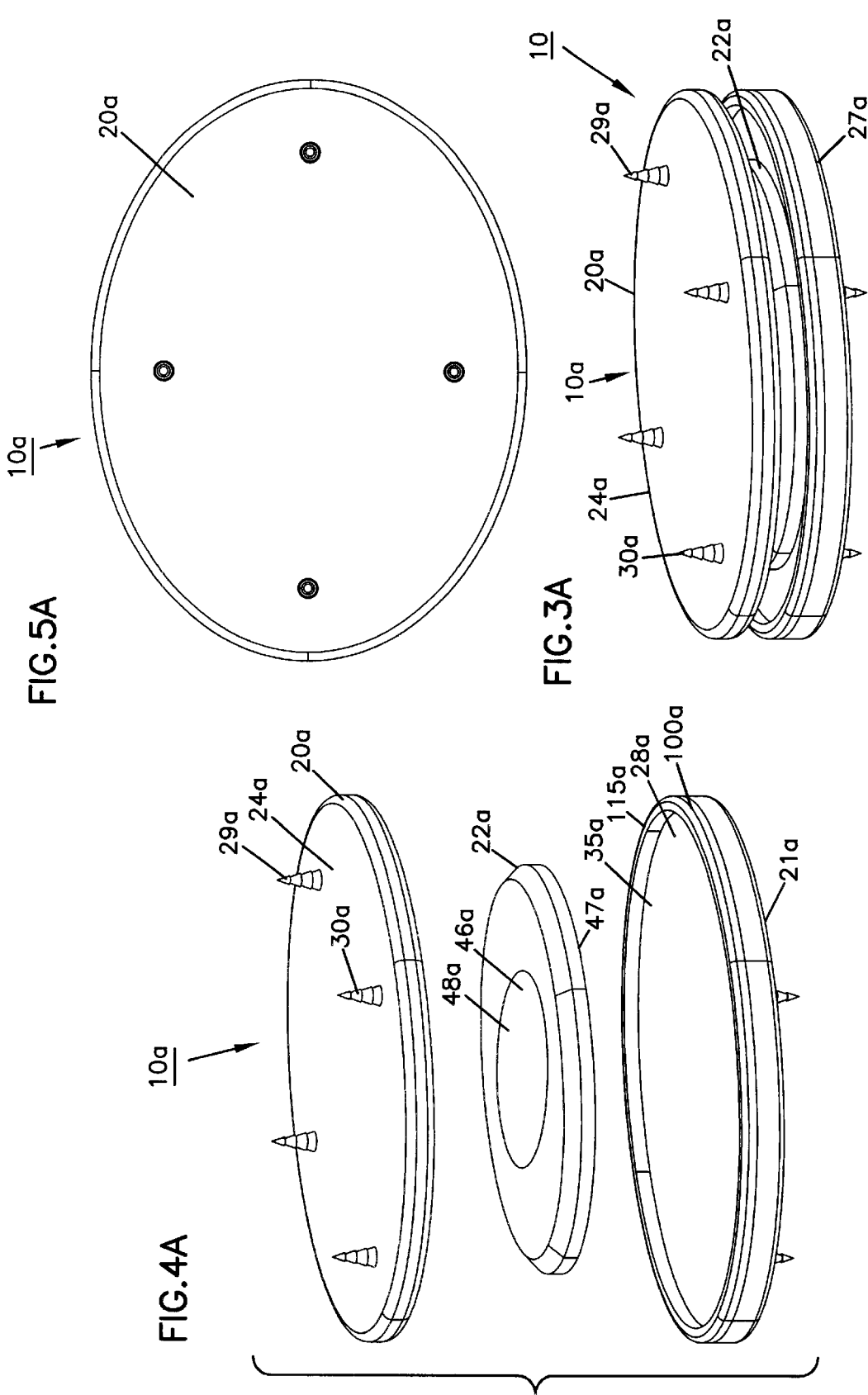

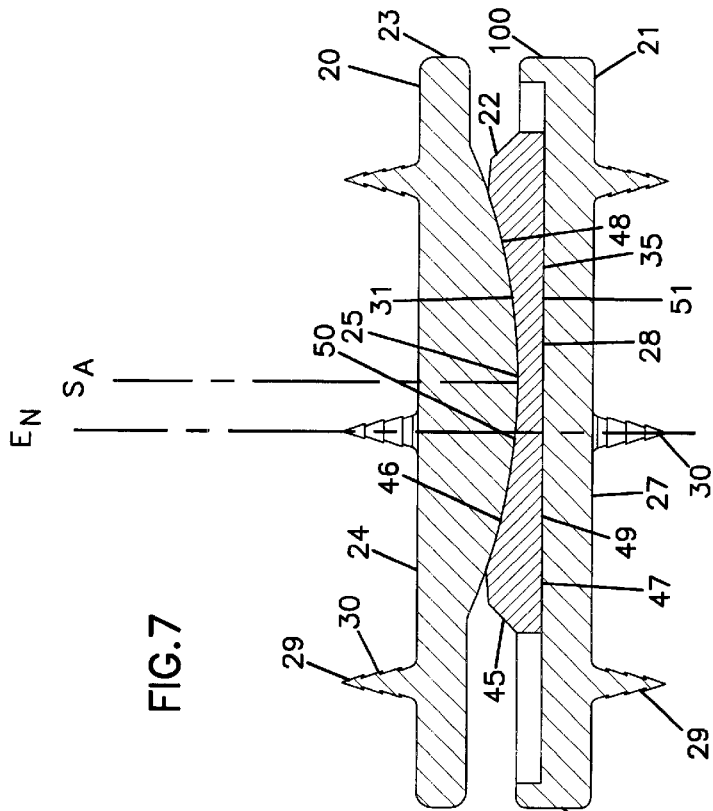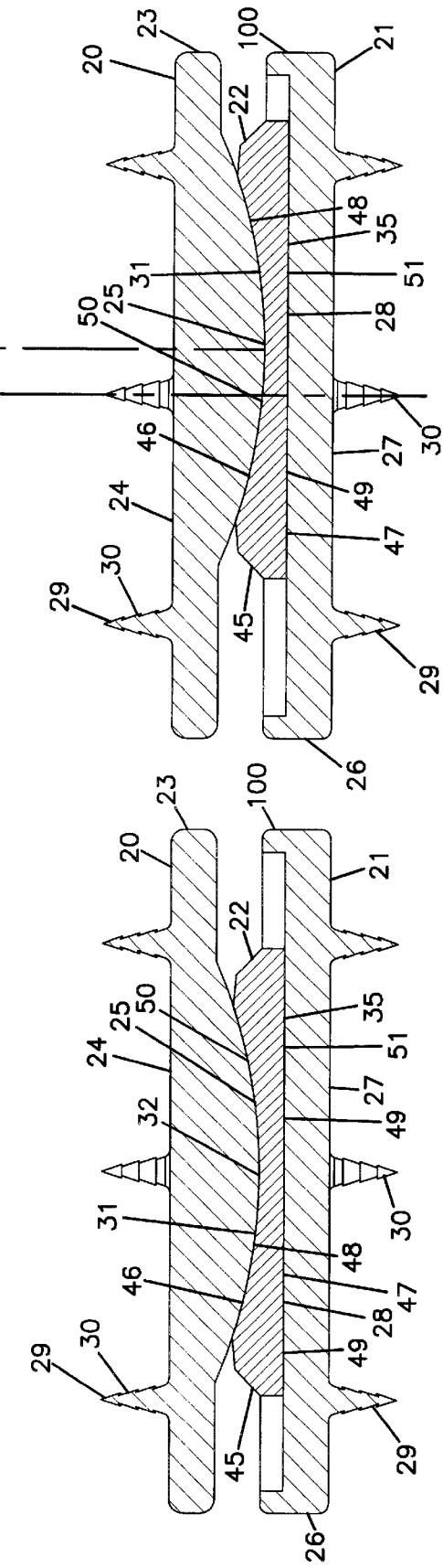

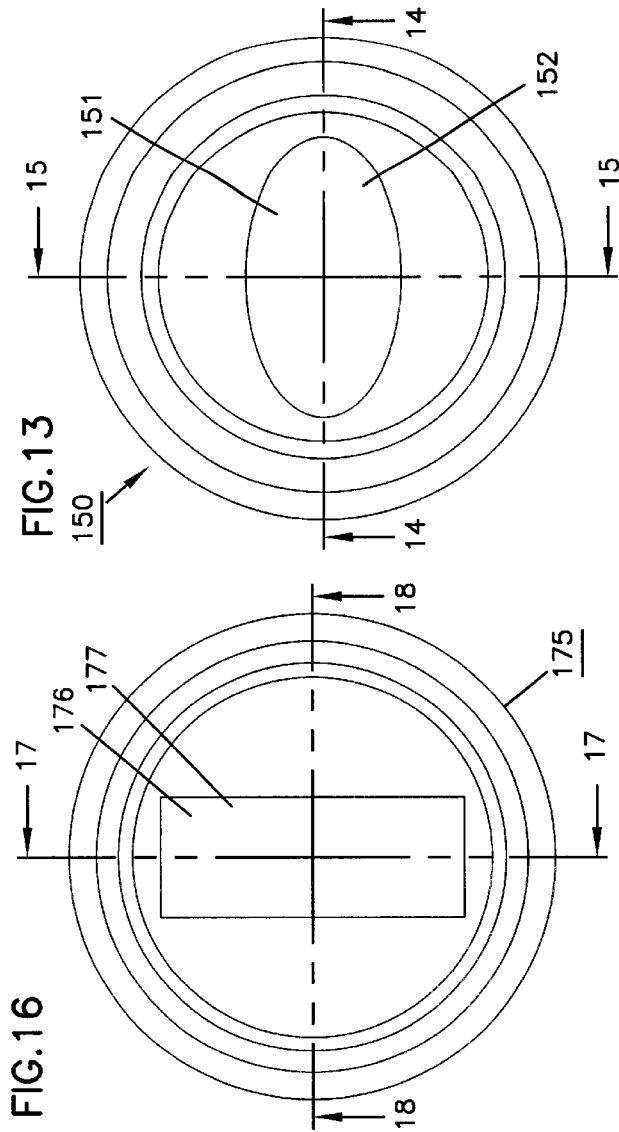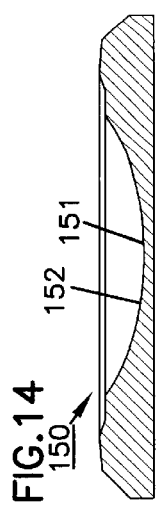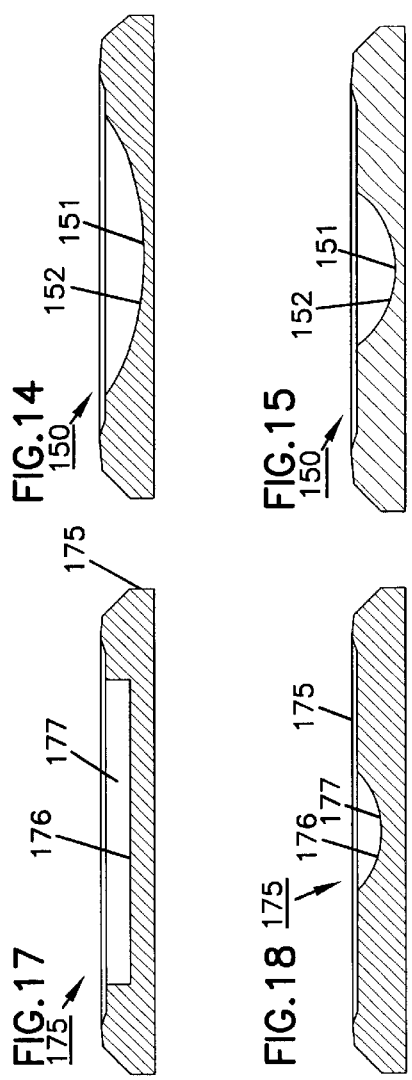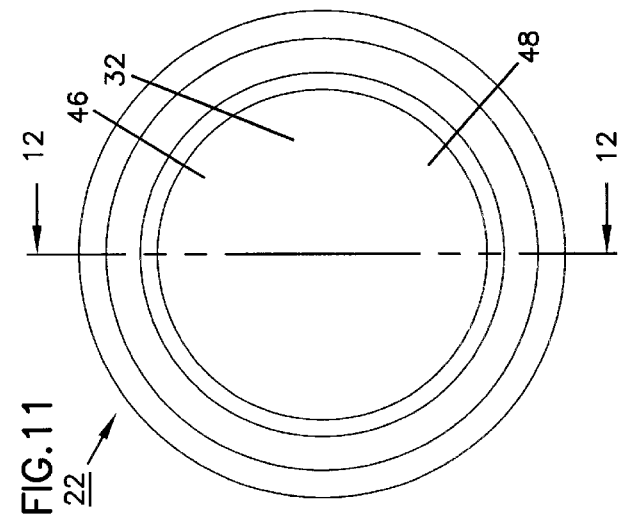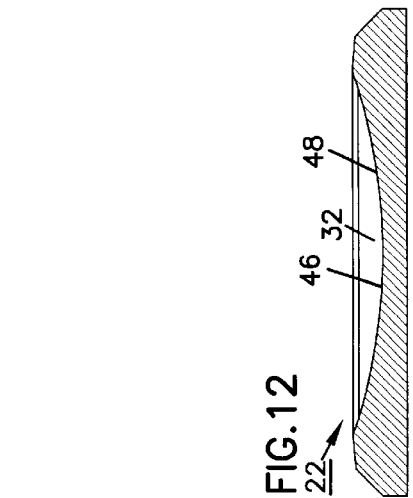

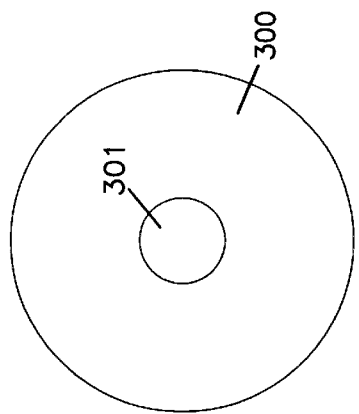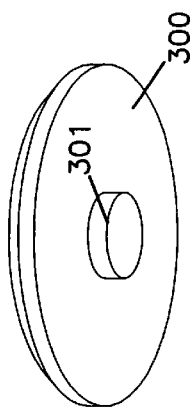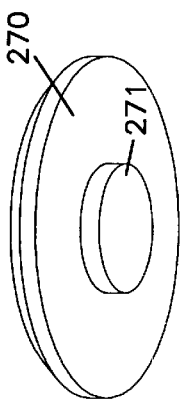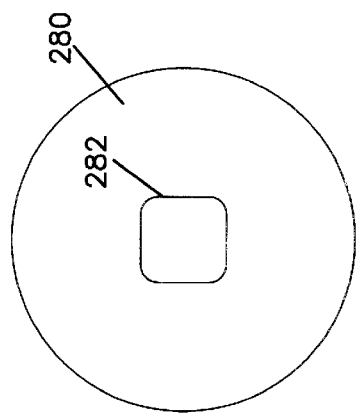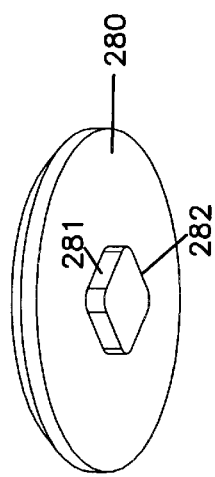

INTERVERTEBRAL DISC PROSTHESIS AND METHOD

FIELD OF THE INVENTION

The present invention pertains to stabilization of an intervertebral disc space. More particularly, the invention pertains to prosthetic intervertebral disc devices and methods for stabilizing an intervertebral disc joint while providing joint mobility.

BACKGROUND OF THE INVENTION

Chronic back problems can cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Arthrodesis of the intervertebral joint can reduce the pain associated with movement of an intervertebral joint having diseased disc material. Generally, fusion techniques involve removal of the diseased disc, drilling a bore for receiving a spinal fusion implant and inserting the implant between the opposing vertebral bodies. Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; and 4,961,740.

One disadvantage to intervertebral disc fusion is that the relative motion between the fused vertebrae is no longer possible, causing both stiffness in the spine and difficulties in the areas above and below the fused vertebrae. Thus, one alternative to fusing a diseased intervertebral joint space is to remove the diseased disc material and replace it with a prosthetic disc. Examples of prosthetic disc devices are disclosed in, for example, U.S. Pat. Nos. 4,759,766; 4,759,769; 5,258,031; 5,401,269; 5,425,773; 5,556,431 and 5,676,701. However, while such devices may provide greater mobility when compared to fused vertebrae, the mobility permitted by most known devices does not fully account for normal vertebral biomechanics.

Accordingly, there is a continuing need for intervertebral stabilization apparatuses and methods which provide mobility at the diseased intervertebral joint space. Moreover, there is a need for intervertebral stabilization methods which mimic normal intervertebral biomechanics.

SUMMARY OF THE INVENTION

The present invention is directed to devices and methods for intervertebral stabilization which provide mobility at the diseased intervertebral joint. One advantageous feature of a device according to the invention is that it mimics normal intervertebral biomechanics by providing a variable instantaneous axis of rotation.

Throughout the specification, guidance may be provided through lists of examples. In each instance, the recited list serves only as a representative group. It is not meant, however, that the list is exclusive.

In general, an intervertebral prosthetic device (IPD) of the invention is an assembly including a first member for contacting a first vertebrae, a second member for contacting a second vertebrae and an intermediate member positioned between the first and second members. The assembly includes at least two bearing surfaces. A first bearing surface formed between the first member and the intermediate member and the second bearing surface formed between the second member and the intermediate member. At least one of the bearing surfaces is curved and at least one of the bearing surfaces is flat. The curved bearing surface can be spherical, cylindrical, ellipsoidal, oblong, etc.

In some embodiments, the curved bearing surface provides at least three degrees of rotational freedom. The linear bearing surface can provide at least two degrees of translational freedom and one degree of rotational freedom. The rotational and translational freedom of an IPD can also be selectively limited through arrangements disclosed herein.

BRIEF DESCRIPTION OF THE DRAWINGS

FIG. 3 is a perspective view of one embodiment of an intervertebral prosthetic device according to the invention;

FIG. 3a is a perspective view of an alternative embodiment of an intervertebral prosthetic device intervertebral prosthetic device according to the invention;

FIG. 4 is an exploded perspective view of the intervertebral prosthetic device of FIG. 3;

FIG. 4a is an exploded perspective view of the intervertebral prosthetic device of FIG. 3a;

FIG. 5 is a top plan view of the intervertebral prosthetic device of FIG. 3;

FIG. 5a is a top plan view of the intervertebral prosthetic device of FIG. 3a;

FIG. 6 is a cross-section view through of the intervertebral prosthetic device of FIG. 5 taken through line 6—6;

FIG. 7 is a cross-section view through the intervertebral prosthetic device of FIG. 5 taken through line 7—7.

FIG. 11 is a top plan view of the intermediate piece of the intervertebral prosthetic device of FIG. 3;

FIG. 12 is a cross-section of the intermediate piece of FIG. 11 through line 12—12;

FIG. 13 is top plan view of an alternative embodiment of an intermediate piece;

FIG. 14 is a longitudinal cross-section view of the intermediate piece of FIG. 13 taken through line 14—14;

FIG. 15 is a transverse cross-section view of the intermediate piece of FIG. 13 taken through line 15—15;

FIG. 16 is a top plan view of an alternative embodiment of an intermediate piece;

FIG. 17 is a longitudinal cross-section view of the intermediate piece of FIG. 16 taken through line 17—17;

FIG. 18 is a transverse cross-section view of the intermediate piece of FIG. 16 taken through line 18—18;

FIG. 22 is a bottom perspective view of the intermediate piece of FIG. 21;

FIG. 25 is a bottom perspective view of an alternative embodiment for an intermediate piece;

FIG. 26 is a bottom plan view of the intermediate piece of FIG. 25;

FIG. 27 is a bottom perspective view of an alternative embodiment of an intermediate piece;

FIG. 28 is a bottom plan view of the intermediate piece of FIG. 27;

DETAILED DESCRIPTION OF THE DISCLOSURE

The present disclosure is directed to intervertebral prosthetic devices and methods which provide rotational and translational movement of an intervertebral joint within physiological constraints. Thus, in many embodiments, the devices and methods disclosed provide intervertebral joint mobility which mimics normal intervertebral joint mobility. In addition to other unique features, the prosthetic devices and methods disclosed provide a variable instantaneous axis of rotation regardless of whether the range of rotational movements is full or limited.

Throughout the disclosure standard terms are used to refer to the orientation and relative location of vertebrae within the vertebral column. The principles, devices and methods disclosed herein are generally applicable to all vertebral mobility. However, for ease of understanding, the invention will be discussed with specific reference to the lumbar vertebrae. Nonetheless, it will be appreciated that the devices and methods disclosed are also applicable for use with cervical and thoracic vertebrae.

Figure 1:
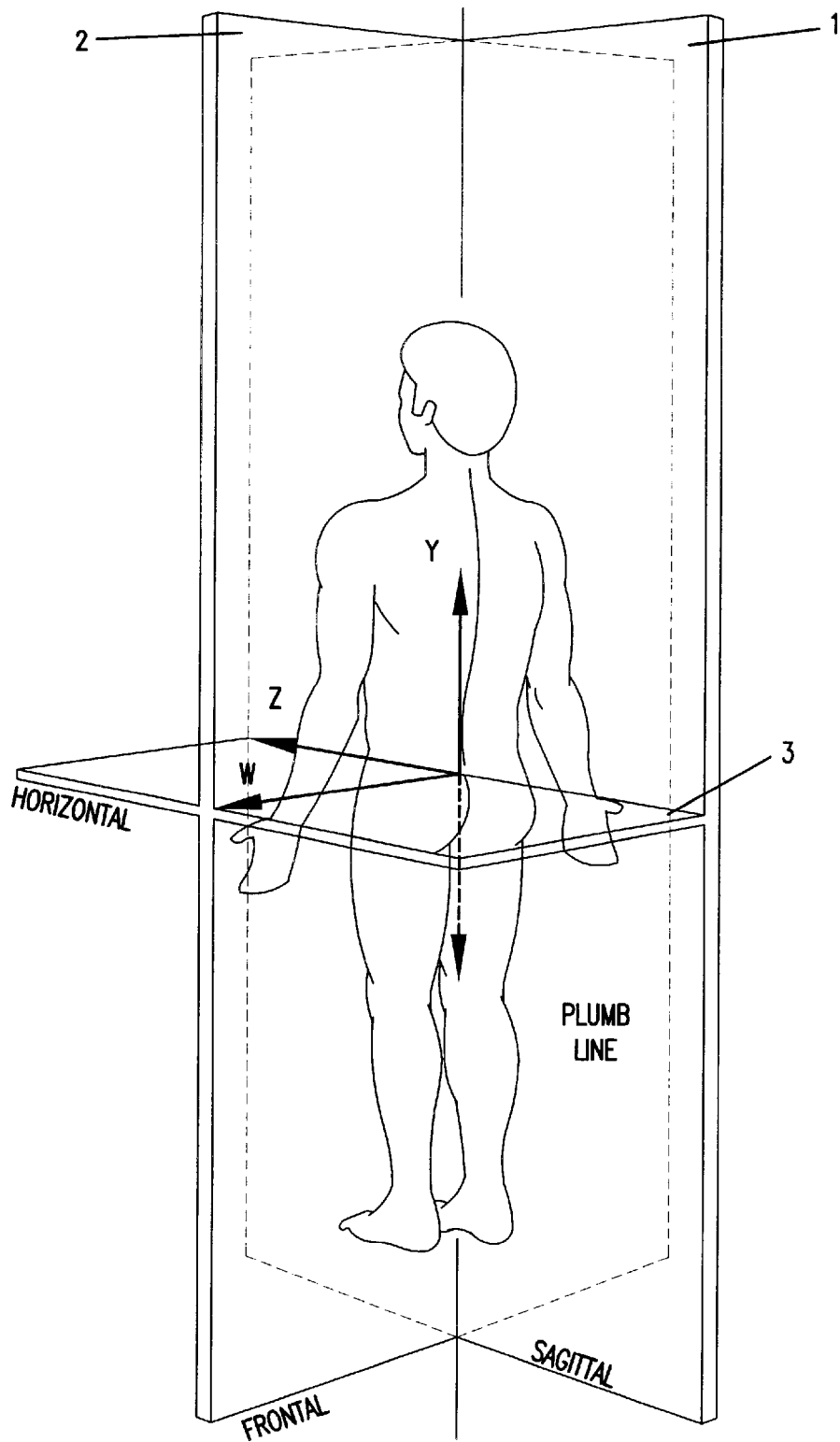
FIG. 1 illustrates standard orientational planes of an XYZ coordinate system for describing rotational and translational movement of the spinal column.

Generally, normal movement between vertebral bodies which are spaced apart by a healthy intervertebral disc includes three types of rotational motion: anterior/posterior rotation (i.e. flexion/extension), lateral rotation (i.e. lateral bending) and axial rotation. FIG. 1 illustrates a human body within standard orientational planes of an x, y, z coordinate system. For purposes here, anterior/posterior rotation (i.e., flexion/extension) is rotation of the vertebral column in the sagittal plane 1. Right and left lateral bending is rotation of the vertebral column in the frontal plane 2 and axial rotation is rotation of the vertebral column around the y axis.

In addition, during rotation, translational movement also occurs. "Translational" movement is the movement which occurs between adjacent vertebrae in horizontal plane, 3. The amount of translational motion which can occur between adjacent vertebrae varies between individuals and, within a given individual, between vertebral body types.

Figure 2B:
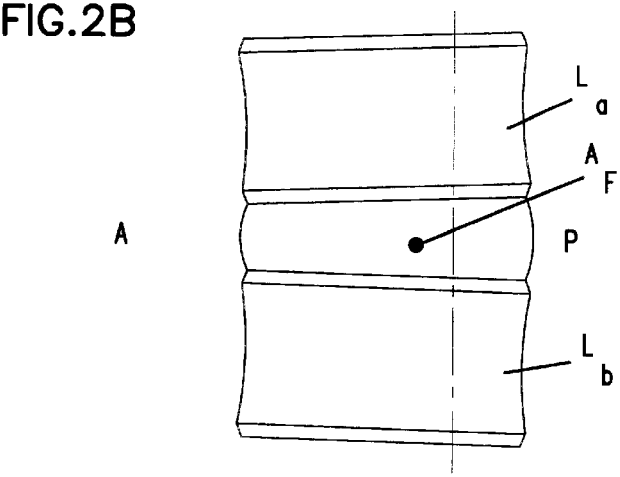
FIGS. 2a–2c diagrammatically illustrate the variable instantaneous axis of rotation which occurs during anterior/posterior rotation of the lumbar vertebrae.
Figure 2A:
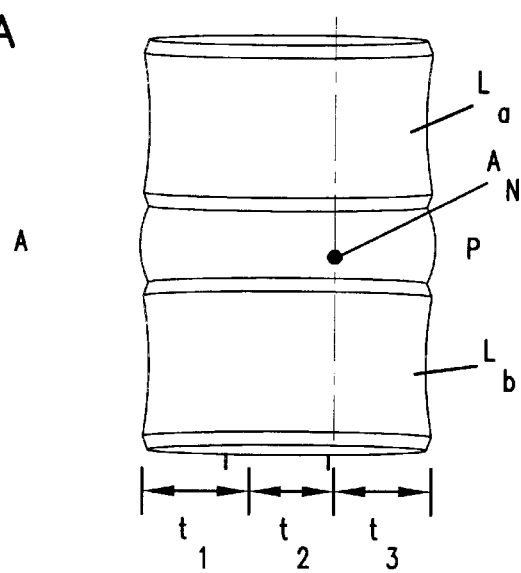
Figure 2C:
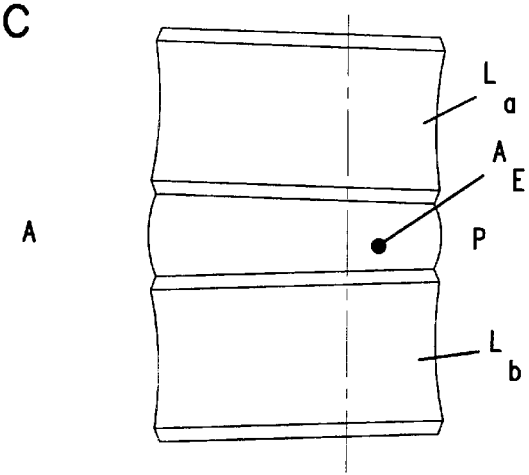

The amount of translational movement which occurs between adjacent vertebrae during each type of rotation is greatest during flexion and extension, minimal during lateral bending, and essentially non-existent during axial rotation. The translational movement which occurs during flexion/extension causes the axis of rotation between adjacent vertebrae to shift anteriorly or posteriorly throughout the anterior/posterior range of motion. FIGS. 2a–2c diagrammatically illustrate an example of the shifting of the axis of rotation between two lumbar vertebrae $L_a$, $L_b$ during flexion/extension. FIG. 2a shows the axis of rotation $A_N$ between adjacent lumbar vertebrae $L_a$ and $L_b$ when in the neutral or standing position. Note that the axis of rotation $A_N$ in this vertebral position is not midway between the anterior (A) and posterior (P) aspects of the vertebrae, but rather is located at about the posterior one third $t_3$ of the vertebrae. FIG. 2b illustrates the position of the axis of rotation $A_F$ during anterior rotation or flexion. FIG. 2c illustrates the position of the axis of rotation $A_E$ during posterior rotation or extension. At each of the positions of FIGS. 2a–2c the location of the axis of rotation has shifted relative to the anterior and posterior aspects of the vertebrae. The shifting of the axis of rotation is a translational movement approximately within the horizontal plane (FIG. 1). Each of the axes illustrated in FIGS. 2a–2c ($A_N$, $A_F$, $A_E$) represent an instantaneous axis of rotation ("IAR"). That is, FIGS. 2a–2c illustrate the axis of rotation between the vertebrae when the vertebrae are in the particular positions illustrated. The shifting location of the rotational axis between vertebrae during relative movement is referred to as a "variable instantaneous axis of rotation."

The intervertebral prosthetic devices and methods disclosed herein mimic the normal movement between adjacent vertebrae by providing a variable instantaneous axis of rotation throughout rotation of the vertebral column, particularly during flexion and extension. The devices and methods disclosed provide greater rotational freedom by permitting at least one degree of translational freedom during rotation. In addition to biomechanical advantages related to patient movement, providing translational freedom throughout rotation reduces the shear forces which occur at the junction between the prosthetic device and the end plates of opposing vertebrae when translational freedom is constrained. Thus, the likelihood of post-surgical expulsion or migration of the device is reduced.

A prosthetic device of the invention includes at least two bearing surfaces provided by three components, two components which attach to adjacent vertebrae and a third component which is positioned between the first two. Each of the first two components or end pieces have a bearing surface and a contact surface. The third component or intermediate piece has at least two bearing surfaces. For clarity, the bearing surfaces of the components of the devices will be referred to as articular surfaces.

In use, the contact surface of each end piece engages the end plate of one of the adjacent vertebrae. Each of the articular surfaces of the intermediate piece are configured to cooperatively fit with the articular surface of one of the end pieces. In general, a first articular surface of the intermediate piece is curved and a second articular surface is planar. The articular surface of the first end piece which is opposed to the first articular surface of the intermediate piece is curved and the articular surface of the second end piece which is opposed to the second articular surface of the intermediate piece is planar. Thus, the prosthetic device includes a curved bearing surface comprised of the curved articular surfaces of one end piece and the intermediate piece and a planar bearing surface comprised of the planar articular surfaces of a second end piece and the intermediate piece.

In some embodiments, the curved bearing surface permits rotational freedom in all directions, that is, rotation around the Y axis, in the sagittal plane, frontal plane and planes oblique to these planes. The planar bearing surface can permit rotational freedom around the Y axis as well as translational freed along the X axis, Z axis and oblique axes therebetween in the horizontal plane 3. Selective limitation of rotational freedom at the curved bearing surface and/or selective limitation of rotational or translational freedom at the planar bearing surface can be provided by configurational arrangements described below.

The curved articular surface of the end piece or intermediate piece can be concave or convex. If the curved articular surface of the intermediate piece is concave, the cooperating articular surface of the end piece will be convex. Alternatively, if the curved articular surface of the intermediate piece is convex, the cooperating articular surface of the end piece will be concave. As used herein, the term "curved" includes configurations such as cylindrical, ellipsoidal, spherical, oblong, etc. As will be discussed, each of these curved configurations affect the type and range of rotational movement which can occur between the vertebral bodies.

The perimeter edge of the linear articular surface of the end piece can be flush or have a protruding lip relative to the articular surface. The configuration of a raised perimeter edge of the end piece and the shape of the linear articular surface of the intermediate piece can be used to affect the freedom of translational or axial rotation at the linear bearing surface. In some embodiments, the raised perimeter edge of the end piece can also affect the rotational range of the curved bearing surface.

The non-bearing or contact surfaces of each of the end pieces can include spikes, porous ingrowth surfaces, contoured surfaces which coaptate with the anatomical surfaces of the vertebral end plate, knurled surfaces, biological surfaces, or other similar arrangement to facilitate anchoring the end piece to the end plate of the vertebral bodies. Alternatively, or additionally, the end pieces of the device can be anchored to the vertebral bodies using bone screws.

In general, the prosthetic devices of the invention are non-compressible. As used herein, "non-compressible" means that the overall height of the device does not change substantially when subjected to the axial forces of patient's body weight. Suitable materials for manufacturing a non-compressible device include metals such as titanium, titanium alloys, stainless steel, cobalt/chromium, etc.; plastics such as poly(ethylene) with ultra high molar mass (molecular weight) (UHMW-PE), polyether ester ketone (PEEK), etc.; ceramics; graphite; etc. The bearing surfaces or articular surfaces can be prepared from metals such as titanium, titanium alloy, stainless steel, cobalt/chromium; plastics such as UHMW-PE, PEEK, etc.; graphite; ceramic; etc. The materials for opposing articular surfaces are preferably selected to minimize the amount of seizing which may occur during movement of the articular surfaces against one another.

Because the devices are non-compressible, providing devices of varying height, measured from the contact surface of a first end piece to the contact surface of the second end piece, permits selecting a device of appropriate height to maintain a desired intervertebral spacing between the vertebrae. The overall height of the device can be varied by increasing or decreasing the thickness of one or more of the first end piece, second end piece and intermediate piece. In addition, in some embodiments, by varying the angulation between the contact surface and the articular surface of one or both end pieces, the prosthetic device can provide a selected degree of lordosis between opposing vertebrae.

The prosthetic devices of the invention will be further described by reference to the following illustrated embodiments. The illustrated embodiments are not intended to limit the scope of the invention, but rather, are provided to facilitate understanding of the devices and methods within the principles of the invention.

DETAILED DESCRIPTION OF THE ILLUSTRATED EMBODIMENT

With reference to the several drawing figures in which identical elements are numbered identically throughout, a description of some embodiments of an intervertebral prosthetic device according to the present invention will now be provided.

FIG. 3 is a perspective view of one embodiment of an intervertebral prosthetic device (IPD) 10 according to the present invention. FIG. 4 is an exploded perspective view of the IPD 10 of FIG. 3 and FIG. 5 is a top plan view. While the perimeter shape of the illustrated IPD is circular, the external configuration of an IPD of the invention can be any shape including, for example, circular, rectangular, square, trapezoidal, oblong, square or trapezoidal with rounded corners, elliptical, kidney bean shaped, etc. FIGS. 3a–5a illustrate an elliptical shaped IPD, the components are identified by the same reference numbers as the device of FIGS. 3–5 but are proceeded by the letter "a."

The IPD 10 includes a first end piece 20 a second end piece 21 and an intermediate piece 22. The IPD 10 can be inserted into an intervertebral disc space between an adjacent cranial and caudal vertebrae such that end piece 20 contacts the cranial vertebrae and end piece 21 contacts the caudal vertebrae. Alternatively, the IPD 10 can be inserted in the intervertebral disc space with second end piece 21 in contact with the cranial vertebrae and first end piece 20 in contact with the caudal vertebrae.

FIG. 6 is a cross-section view taken through the IPD 10 of FIG. 5 at line 6—6. FIG. 7 is a cross-section view taken through line 7—7. If inserted in an intervertebral space of a patient, FIG. 7 would be a left lateral view.

As seen in FIGS. 6 and 7, the first end piece 20 includes a first end base 23 having a first end contact surface 24 and a first end articular surface 25. Similarly, second end piece 21 includes a second end base 26 having a second end contact surface 27 and a second end articular surface 28. In FIGS. 3–7, the contact surfaces 24 and 27 include an anchoring arrangement 29 for fixing the end piece to the end plates of a vertebral body. The illustrated anchoring arrangement 29 includes spikes 30 which can be embedded into the vertebral end plates to anchor device 10 to the vertebrae. Alternative anchoring arrangements 29 at contact surfaces 24 and 27 include porous coated ingrowth surfaces, knurled surfaces, contoured or textured surfaces, biological coatings (e.g., peptide coatings, etc.), etc. Bone cement, osteoconductive materials, osteoconductive materials, and other known systems can also be used to facilitate anchoring an IPD to the end plates of adjacent vertebrae. In addition, as discussed below, bone screws can be used to fix the end pieces to the vertebrae.

In the embodiment of FIGS. 3–7, the first end articular surface 25 is a convex curved surface 31. The second end articular surface 28 is a planar surface 35. A raised edge 100 is provided around the perimeter of second end articular surface 28. As best seen in FIGS. 6 and 7, first end articular surface 31 can be spherical 32. As best appreciated in FIG. 7, although the first end piece 20 and first end articular surface 31 both have circular perimeters, the central axis $E_A$ of the first end piece 20 need not be coaxial with the central axis $S_A$ of the first end piece articular surface 31.

The intermediate piece 22 includes an intermediate base 45, a first intermediate articular surface 46 and second intermediate articular surface 47. The first intermediate articular surface 46 is a concave curve 48 and the second intermediate articular surface 47 is planar 49. As stated above, in alternative embodiments, the concave curved surface can be a part of the end piece and the convex curved surface can be a part of the intermediate piece.

Thus, when components 20, 21, 22 are assembled, the first intermediate articular surface 46 cooperatively articulates with first end articular surface 25 forming first assembly bearing surface 50. The second intermediate articular surface 47 cooperatively articulates with second end articular surface 28 forming second assembly bearing surface 51. In the illustrated embodiment, the first assembly bearing surface 50 is curved and the second assembly bearing surface 51 is planar.

The curved assembly bearing surface 50 allows at least three degrees of rotational freedom unconstrained throughout the anatomical range of motion between the vertebral bodies. The second assembly bearing surface 51 allows at least two degrees of translational freedom and one degree of rotational freedom. That is, curved assembly bearing surface 50 provides for anterior/posterior rotation (flexion/extension) in a sagittal plane 1 (see FIG. 1), lateral rotation (lateral bending) in a frontal plane 2 and axial rotation along the Y axis. Rotational motion can also occur in planes oblique to the sagittal 1 and frontal 2 planes. Planar assembly bearing surface 51 provides translational motion in horizontal plane 3 along the Z axis and X axis and rotational motion about the Y axis. Translational motion can also occur along axes oblique to the X and Z axes in the horizontal plane 3.

Figure 8:
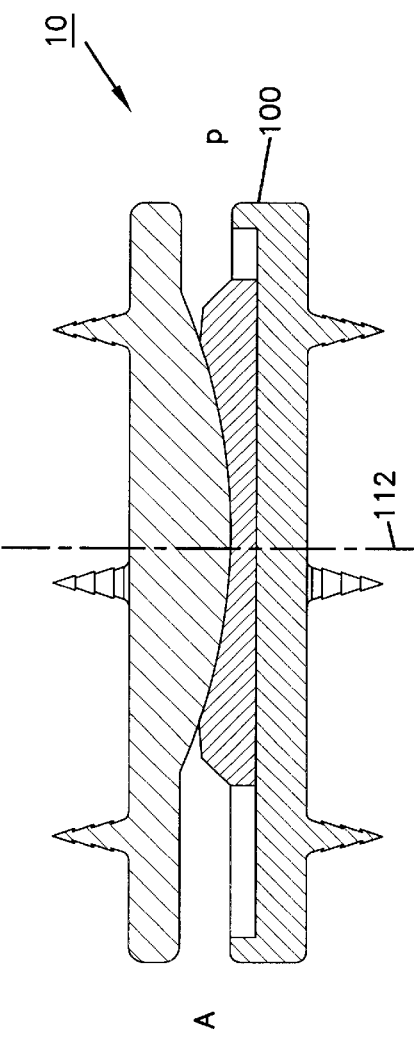
FIG. 8 is a cross-section of the intervertebral prosthetic device of FIG. 5 taken through line 7—7 as viewed from the left lateral aspect of a patient when in the neutral (standing) position.
Figure 10:
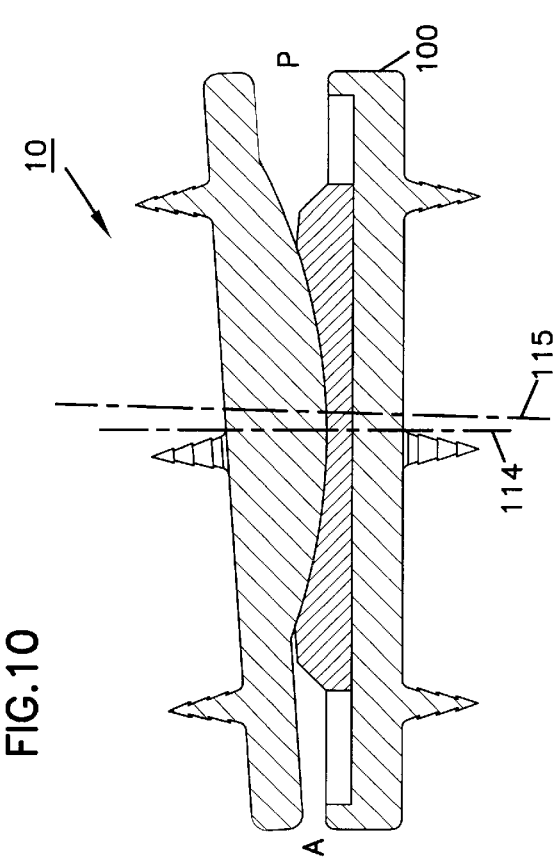
FIG. 10 is the same view as FIG. 8 but when in flexion (anterior rotation)
Figure 9:
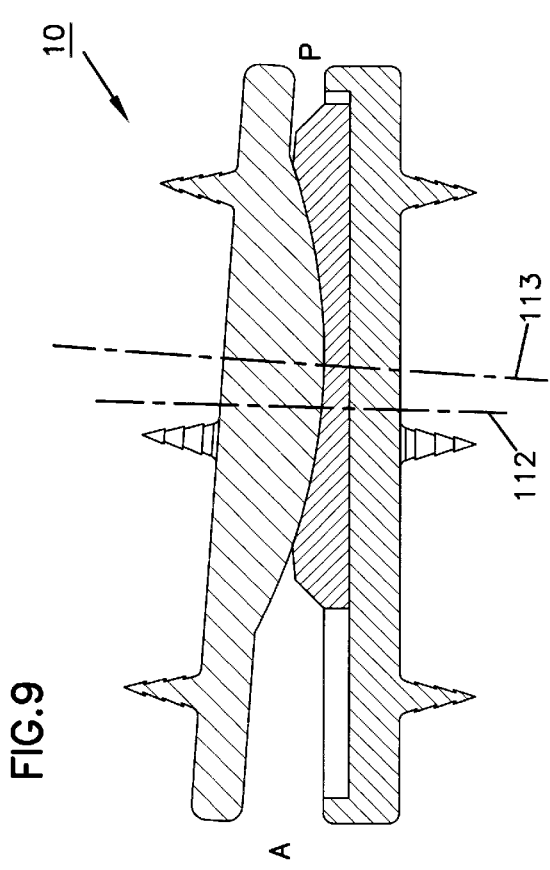
FIG. 9 is the same view as FIG. 8 but when in extension (posterior rotation)

Referring now to FIGS. 8–10, the variable instantaneous axis of rotation provided by an IPD of the invention during vertebral movement will be described. FIGS. 8–10 are sagittal cross-section views taken through 7—7 of FIG. 5, viewed from the patient's left side. In FIG. 8, the IPD 10 is shown when the patient is in the neutral or standing position. The instantaneous axis of rotation (IAR) at this position is at line 112. In FIG. 9, during extension (posterior rotation), the IAR shifts posteriorly to position 113. In FIG. 10, during flexion (anterior rotation), the IAR shifts anteriorly to position 114. Thus, the translational freedom provided by flat bearing surface 51 readily permits the IAR to shift as dictated by the change in the relative positions of the adjacent vertebrae. This translational freedom provides a variable instantaneous axis of rotation. In addition to the anterior/posterior translational freedom illustrated in FIGS. 8–10, flat bearing surface 51 also permits translational freedom in a lateral direction as well as in any other direction within horizontal plane 3 of FIG. 1. As will be discussed below, limiting arrangements such as raised edge 100 can be configured to limit the rotational or translational freedom provided at the planar bearing surface 51. Before addressing limitations to rotational freedom, however, configurations for limiting certain rotational freedoms will be discussed.

FIG. 11 is a top view of intermediate piece 22 of FIG. 3 and FIG. 12 is a cross-section view of FIG. 11. The concave curve 48 of first intermediate articular surface 46 is spherical 32. This concave spherical surface 32 permits a convex articular surface 25 of first end piece 20 to rotate freely in a sagittal plane, frontal plane or around the Y axis.

In an alternative embodiment of an intermediate piece 150 illustrated in FIGS. 13–15, the concave surface 151 is ellipsoidal 152. The longitudinal cross-section of FIG. 14 is taken through line 14—14 of FIG. 13 and the transverse cross-section of FIG. 15 is taken through line 15—15. When intermediate piece 150 is oriented within an IPD with long dimensions 14—14 parallel to the frontal plane 2, the ellipsoidal surface 152 will permit substantially full anterior/posterior rotation, but lateral rotation will be limited. If long dimension 14—14 is oriented parallel to sagittal plane 1, lateral rotation will be substantially free and anterior posterior rotation limited. According to this embodiment, the cooperating articular surface is preferably also ellipsoidal.

FIGS. 16–18 show another embodiment of an intermediate piece which limits rotational motion to a single plane at the curved bearing surface 50. As seen in top view of FIG. 16, intermediate piece 175, has a curved bearing surface 176 which is cylindrical 177. FIG. 17 is a long dimension cross-section taken through line 17—17 of FIG. 16 and FIG. 18 is a transverse cross-section view taken through line 18—18 of FIG. 16. This configuration limits lateral rotation when long dimension 17—17 is oriented parallel to the frontal plane 2 and limits anterior/posterior rotation when long dimension 17—17 is oriented parallel to the sagittal plane 1.

Figure 19:
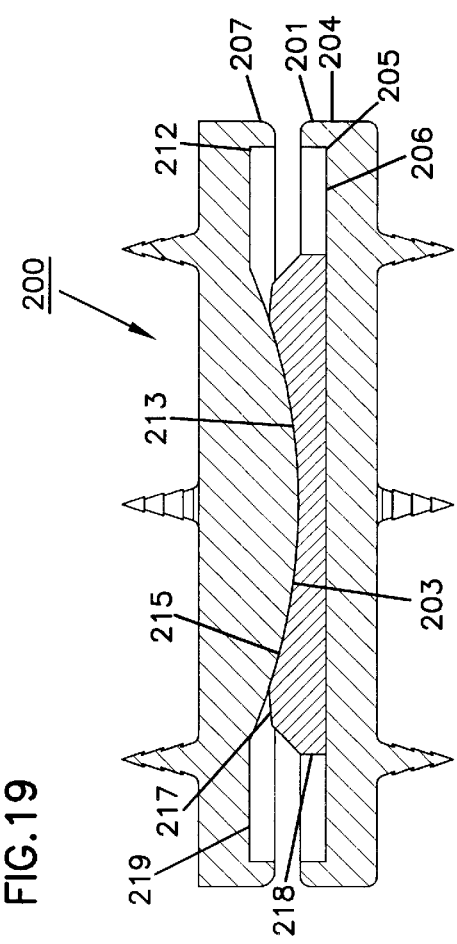
FIG. 19 is a cross-section through an alternative embodiment of an intervertebral prosthetic device according to the invention.

FIG. 19 is a cross-section view through an alternative embodiment of an IPD 200 showing an alternative limiting arrangement 201 for limiting rotation of curved bearing surface 203. According to this embodiment, a raised lip 204 is present around the perimeter edge 205 of planar articular surface 206. In addition, a raised lip 207 is also present at the perimeter edge 212 surrounding curved articular surface 213. Thus, in the embodiment of FIG. 19, lip 204 not only limits translational motion at the perimeter edge 201 of the planar articular surface 206, but also, rotation of curved articular surface 213 is limited when lip 204 meets lip 207. In addition, rotation at curved bearing surface 215 is also limited when flange 217 of intermediate piece 218 contacts flat perimeter surface 219 surrounding curved articular surface 213. Similar limiting effects can be obtained by positioning one or more raised stops in place of the illustrated lip.

Figure 21:
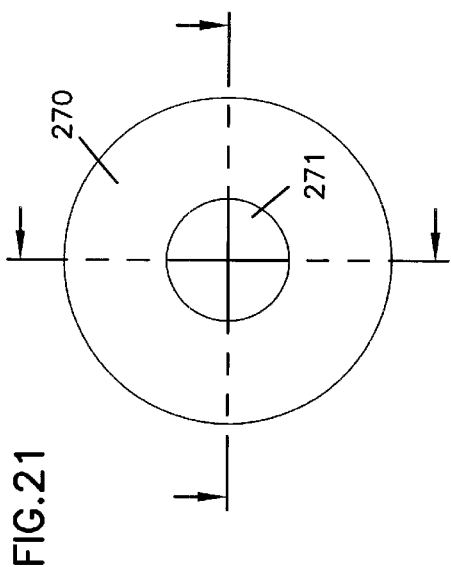
FIG. 21 is a bottom plan view of one embodiment of an intermediate piece which cooperatively articulates with the end piece of FIG. 20.
Figure 20:
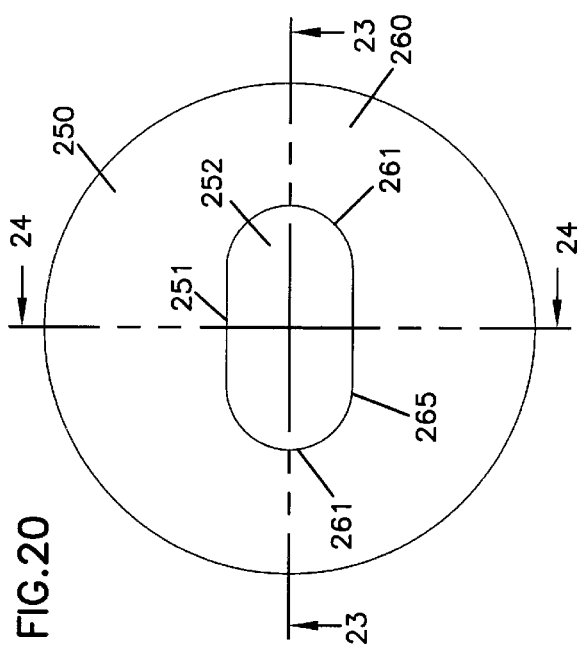
FIG. 20 is a top plan view of an alternative embodiment of the linear surface of an end piece of an intervertebral prosthetic device of the invention.

Translational freedom of an IPD can also be limited at the flat bearing surface. Referring to FIGS. 20–24, in one embodiment, raised perimeter edge 250 of end piece 260 can be configured such that the edge 250 forms a track 251 around flat articular surface 252 as illustrated in the top plan view of FIG. 20. FIG. 21 is a bottom plan view of an intermediate piece 270 having a peg 271, best illustrated in the bottom perspective view of FIG. 22. In this embodiment, translational rotation is limited to one degree as peg 271 travels in track 251 of end piece 260. The short sides 261 at the ends of long dimension 23—23 of track 251 do not need to be present to limit the translational freedom described for this embodiment.

Figure 23:
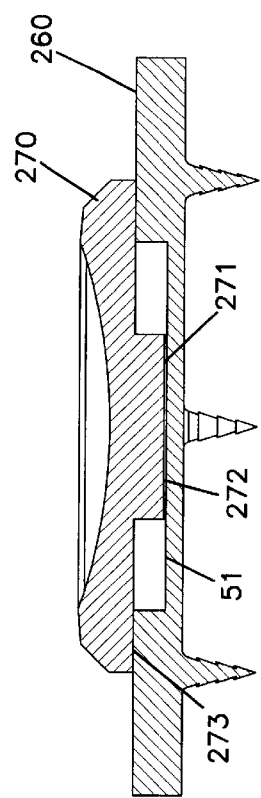
FIG. 23 is a longitudinal cross-section view through the end piece of FIG. 20 and intermediate piece of FIG. 22 when in cooperating arrangement.
Figure 24:
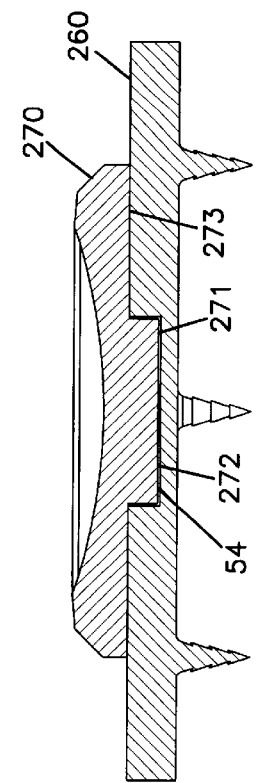
FIG. 24 is a transverse cross-section view through the end piece and intermediate piece when in cooperating arrangement as in FIG. 23.

FIG. 23 is a cross-section through the long dimension 23—23 of track 251 when intermediate piece 270 is in cooperating relationship with end piece 250. FIG. 24 is a transverse cross-section through line 24—24 of the same cooperative arrangement as FIG. 23. Rotational freedom at the flat articular surface is not limited. As illustrated in FIGS. 23 and 24, in this embodiment, the flat bearing surface 51 includes articulating surfaces 272 and 273 at two levels.

Referring to the embodiment of intermediate piece 280 in FIGS. 25 and 26, when intermediate piece 280 is in cooperative arrangement with end piece 250, the linear edges 281 of peg 282 are guided by the edges of track 251 to limit axial rotation in addition to limiting one degree of translational freedom.

In yet another embodiment, FIG. 27 illustrates an intermediate piece 300 substantially similar to intermediate piece 270 of FIG. 21. However, as illustrated in FIG. 28, in this embodiment the diameter of peg 301 is less than the width of track 251 of end piece 260. Thus, when intermediate piece 300 and end piece 260 are in cooperating arrangement, intermediate piece 300 has the same translational freedom as intermediate piece 270 in long dimension 23—23, but, due to the smaller diameter of peg 301, intermediate piece 300 has an increased lateral translational freedom.

Various configurations of "tracks" and "pegs" will be apparent which are within the scope of the invention and which can be combined to provide a particular type of limitation to motion. For example, the elliptically shaped perimeter of an intermediate piece 22a, such as illustrated in FIG. 4a, can be cooperatively arranged with an appropriately sized track, such as an oblong track 265 of FIG. 20 to provide substantially full translational freedom along long dimension 23—23 and some degree of rotational freedom due to the narrowing at the long dimension ends of an elliptical intermediate piece 22a. Increased lateral freedom can also be provided by making the short dimension of elliptical intermediate piece 22a less than the short dimension through line 24—24 of oblong track 265.

Figure 29:
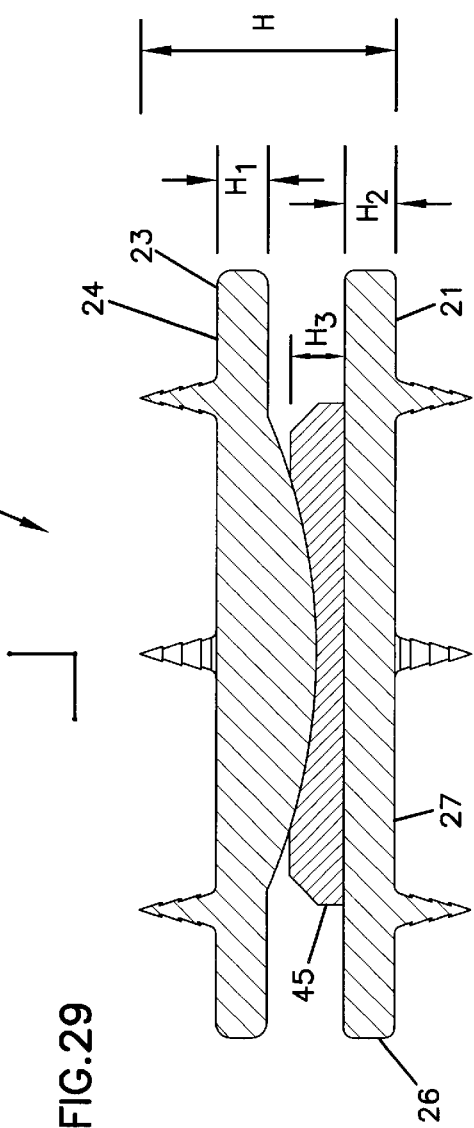
FIG. 29 is a diagrammatic side view of an intervertebral disc prosthesis.

Referring to FIG. 29, it will be appreciated that an IPD such as IPD 10 has an overall height dimension H extending from first end contact surface 24 to second end contact surface 27. The height dimension H can be varied by varying one or more of the height dimensions of first end base 23 ($H_1$), intermediate base 45 ($H_3$) or second end base 26 ($H_2$). By providing IPDs 10 having various height dimensions H, an IPD 10 of selected height can be used for a desired intervertebral spacing between adjacent vertebrae.

Figure 30:
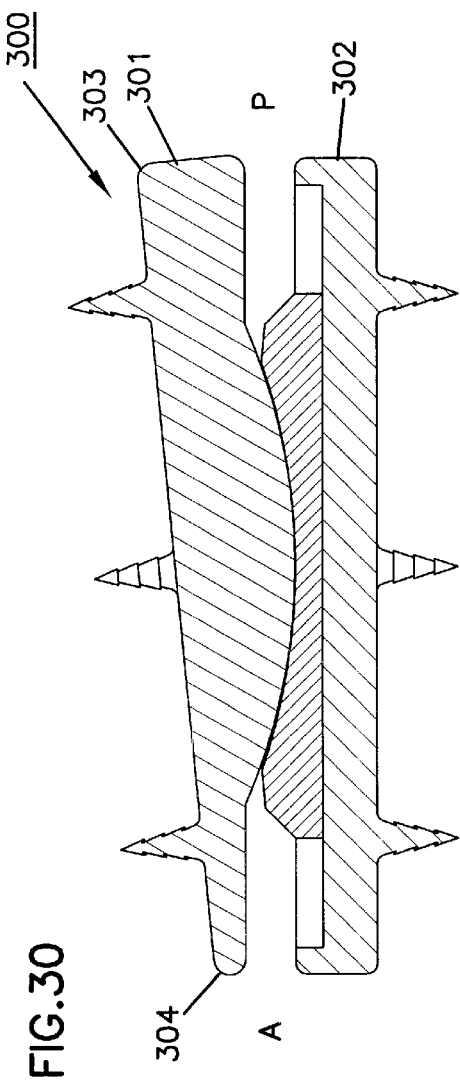
FIG. 30 is a cross-section view through a first embodiment of a lordotic intervertebral prosthetic device.
Figure 31:
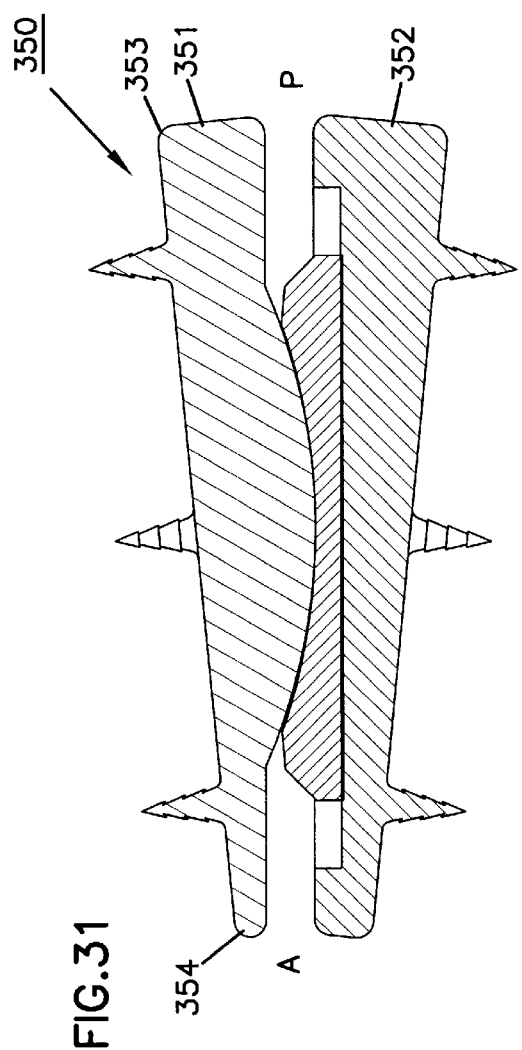
FIG. 31 is a cross-section view through an alternative embodiment of a lordotic intervertebral prosthetic device.

FIGS. 30 and 31 are cross-section views of two alternative embodiments of an IPD for creating a selected degree of lordosis between adjacent vertebrae. IPD 300 of FIG. 30 includes a first end piece 301 having a taper to provide the desired degree of lordosis. In this embodiment, second end piece 302 does not include a taper. The taper of first end piece 301 from edge 303 to edge 304 can be approximately 0–22°. Referring to the IPD 350 of FIG. 31, both first end piece 351 and second end piece 352 have a taper from edge 353 to edge 354. The combined IPD taper from edge 353 to edge 354 can be about 0–22°.

Figure 32:
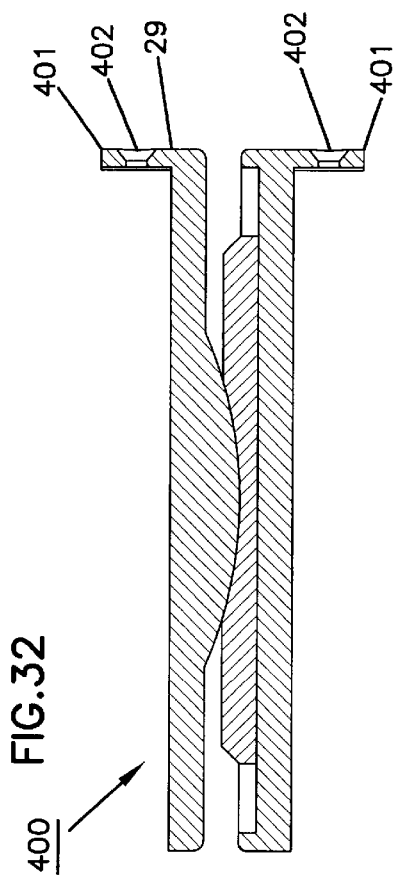
FIG. 32 is a cross-section view through another embodiment of an intervertebral prosthetic device of the invention.
Figure 33:
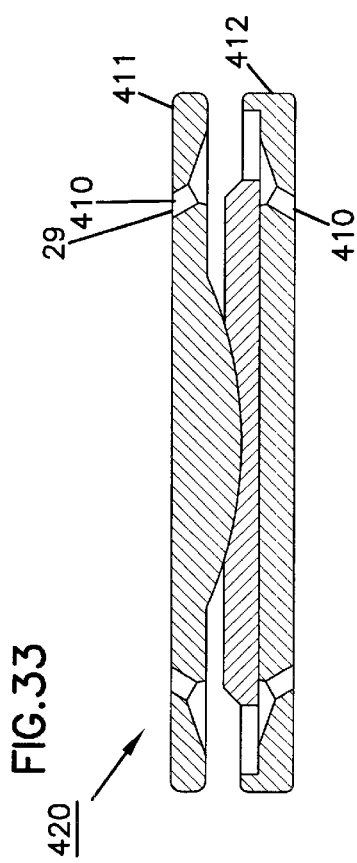
FIG. 33 is a cross-section view through another embodiment of an intervertebral prosthetic device of the invention.

FIGS. 32 and 33 illustrate IPDs 400 and 420 having two different anchoring arrangements 29 which can be used alone, in combination with one another, or in combination with other anchoring arrangements. In FIG. 32, anchoring arrangement 29 comprises an anchoring tab 401 having bores 402 through which lag screws can be passed into the anterior surface of the vertebrae. In FIG. 33, end pieces 410 and 411 each have bores 412 through which lag screws can be passed to anchor the IPD to the end plates of the vertebrae.

Generally, the materials of an IPD are non-compressible. That is, the materials render the IPD substantially resistant to axial compression by the weight of the patient into which the device is inserted. Examples of suitable materials were described above. Combinations of materials can also be used in a single IPD. For example, in one embodiment, an IPD can include a first end piece and second end piece manufactured from titanium and an intermediate piece manufactured from UHMW-PE, PEEK, or other suitable plastic. In an alternative embodiment, an IPD can include a first and second end piece manufactured from cobalt/chromium with an intermediate piece manufactured from UHMW-PE, PEEK or other plastic. In yet another alternative, each of the first end piece, second piece and intermediate piece can be manufactured from cobalt/chromium.

Known methods for insertion of intervertebral prosthetic devices can be used for insertion of an IPD according to the invention. Typically, the surgical procedure for insertion of an IPD into the intervertebral disc space will be performed through an anterior, lateral or anterior-lateral approach.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

We claim:

1. An intervertebral disc prosthesis for placement between first and second adjacent vertebrae, comprising:
   a first end member for contacting the first vertebra, said first end member having a first flat surface;
   a second end member for contacting the second vertebra, said second end member having a first curved surface, wherein said second end member has a central axis and said first curved surface has a central axis and said central axes are not coaxial;
   an intermediate member having an intermediate flat surface and an intermediate curved surface such that said intermediate flat surface coaptates with said first flat surface to provide at least two degrees of translational freedom and said intermediate curved surface coaptates with said first curved surface.

2. The intervertebral disc prosthesis according to claim 1 wherein said first curved surface is concave and said intermediate curved surface is convex.

3. The intervertebral disc prosthesis according to claim 1 wherein said first curved surface is convex and said intermediate curved surface is concave.

4. The intervertebral disc prosthesis according to claim 1 wherein said intermediate curved surface is spherical.

5. The intervertebral disc prosthesis according to claim 1 wherein said intermediate curved surface is ellipsoidal.

6. The intervertebral disc prosthesis according to claim 5 wherein when inserted between the adjacent vertebrae said ellipsoidal surface has a long axis which is parallel to a frontal plane.

7. The intervertebral disc prosthesis according to claim 1 wherein said intermediate curved surface is cylindrical.

8. The intervertebral disc prosthesis according to claim 1 wherein said first flat surface includes a raised perimeter edge.

9. The intervertebral disc prosthesis according to claim 1 wherein said first and second end members each include a first and second contact surface, respectively, each of said contact surfaces having an anchoring arrangement for attaching said prosthesis to the vertebrae.

10. The intervertebral disc prosthesis according to claim 9 wherein said anchoring arrangement includes at least one spike.

11. The intervertebral disc prosthesis according to claim 1 wherein said prosthesis includes bores for passing screws for anchoring said prosthesis to said first and second vertebrae.

12. The intervertebral disc prosthesis according to claim 1 wherein said prosthesis includes cobalt/chromium.

13. The intervertebral disc prosthesis according to claim 1 wherein said prosthesis includes plastic.

14. The intervertebral disc prosthesis according to claim 1 wherein said prosthesis includes ceramic.

15. The intervertebral disc prosthesis according to claim 1 wherein said prosthesis includes graphite.

16. The intervertebral disc prosthesis according to claim 1 wherein said first flat surface, first curved surface, intermediate flat surface and intermediate curved surface include cobalt/chromium.

17. An intervertebral prosthetic device for placement between first and second adjacent vertebrae, comprising:
    a first end piece for engaging said first vertebra;
    a second end piece for engaging said second vertebra; and
    a center piece which fits between said first and second end pieces, said center piece providing a variable instantaneous axis of rotation and including a curved surface and a flat surface such that between said first end piece and said flat surface of said center piece, said device can rotate around an axis oriented perpendicular to said flat surface, wherein said curved surface of said center piece is cylindrical or ellipsoidal.

18. The intervertebral prosthesis device according to claim 17 wherein said curved surface is ellipsoidal.

19. The intervertebral prosthesis device according to claim 17 wherein said curved surface and flat surface includes cobalt/chromium.

20. An intervertebral prosthetic device for placement between first and second adjacent vertebrae, comprising:
    a first end piece for engaging said first vertebra;
    a second end piece for engaging said second vertebra; and
    a center piece which fits between said first and second end pieces, said center piece providing at least two degrees of linear translational freedom during vertebral rotation, wherein said first end piece comprises a flat surface having a raised perimeter edge.

21. The intervertebral prosthetic device according to claim 20 wherein said device provides at least three degrees of rotational freedom and at least two degrees of translational freedom.

22. A non-compressible intervertebral disc device for placement between first and second adjacent vertebrae, comprising:
    a first bearing surface providing at least one degree of rotational freedom, wherein said first bearing surface is cylindrical or ellipsoidal;
    a second bearing surface providing at least one degree of linear translational freedom and rotational freedom around an axis passing through said first and second bearing surfaces.

23. The intervertebral disc device according to claim 22 wherein said first bearing surface provides at least three degrees of rotational freedom.

24. The intervertebral disc device according to claim 22 wherein said second bearing surface provides at least two degrees of linear translational freedom.

25. A non-compressible intervertebral disc device for placement between first and second adjacent vertebrae, comprising:
    a first bearing surface, a second bearing surface providing a variable instantaneous axis of rotation and at least one degree of rotational freedom at each of said first and second bearing surfaces around an axis passed through said first and second bearing surfaces, at least one of said first and second bearing surfaces being cylindrical or ellipsoidal.

26. The non-compressible intervertebral disc device according to claim 25 wherein said second bearing surface provides at least one degree of translational freedom.

27. A method for providing intervertebral mobility between adjacent first and second vertebrae comprising a step of:
    inserting into an intervertebral space between said adjacent first and second vertebrae a non-compressible prosthetic device having at least two degrees of translational freedom which provides a variable instantaneous axis of rotation, wherein said non-compressible prosthetic device comprises
    a first end piece for engaging said first vertebra;
    a second end piece for engaging said second vertebra; and
    a center piece which fits between said first and second end pieces, said center piece providing a variable instantaneous axis of rotation and including a curved surface and a flat surface such that between said first end piece and said flat surface of said center piece, said device can rotate around an axis oriented perpendicular to said flat surface, wherein said curved surface of said center piece is cylindrical or ellipsoidal.

28. A method for providing intervertebral mobility between adjacent first and second vertebrae comprising a step of:
    inserting into an intervertebral space between said adjacent first and second vertebrae a non-compressible prosthetic device which provides at least two degrees of translational mobility between said adjacent vertebrae during rotation, wherein said non-compressible prosthetic device comprises
    a first end piece for engaging said first vertebra;
    a second end piece for engaging said second vertebra; and
    a center piece which fits between said first and second end pieces, said center piece providing a variable instantaneous axis of rotation and including a curved surface and a flat surface such that between said first end piece and said flat surface of said center piece, said device can rotate around an axis perpendicular to said flat surface, wherein said curved surface of said center piece is cylindrical or ellipsoidal.

29. A method for providing intervertebral mobility between adjacent first and second vertebrae comprising a step of:
    inserting into an intervertebral space between said adjacent first and second vertebrae a non-compressible prosthetic device having a first bearing surface and a second bearing surface wherein said second bearing surface provides translational freedom in an anterior/posterior direction and in a lateral direction and said translational freedom is confined by a raised perimeter edge, wherein said non-compressible prosthetic device comprises
    a first end piece for engaging said first vertebra;
    a second end piece for engaging said second vertebra; and
    a center piece which fits between said first and second end pieces, said center piece providing a variable instantaneous axis of rotation and including a curved surface and a flat surface such that between said first end piece and flat surface of said center piece, wherein said curved surface of said center piece is cylindrical or ellipsoidal.

* * * * *

UNITED STATES PATENT AND TRADEMARK OFFICE
CERTIFICATE OF CORRECTION

PATENT NO. : 6,368,350 B1
DATED : April 9, 2002
INVENTOR(S) : Erickson et al.

It is certified that error appears in the above-identified patent and that said Letters Patent is hereby corrected as shown below:

Column 6,
Lines 64-65, "osteoconductive materials, osteoconductive materials" should read
-- osteoconductive materials, osteoinductive materials --

Signed and Sealed this

Thirty-first Day of December, 2002

JAMES E. ROGAN
*Director of the United States Patent and Trademark Office*